United States Patent [19]

Hession et al.

[11] Patent Number: 5,217,870
[45] Date of Patent: Jun. 8, 1993

[54] MONOCLONAL ANTIBODIES AGAINST CDX

[75] Inventors: Catherine A. Hession, South Weymouth; Roy R. Lobb, Westwood; Susan E. Goelz, Winchester, all of Mass.

[73] Assignee: Biogen, Inc., Cambridge, Mass.

[21] Appl. No.: 345,151

[22] Filed: Apr. 28, 1989

[51] Int. Cl.$^5$ .................. C07K 15/28; C12N 5/20
[52] U.S. Cl. .................. 435/7.24; 435/172.2; 435/240.27; 530/388.7
[58] Field of Search .............. 530/387, 809, 388.7; 435/7.23, 7.24, 172.2, 240.27; 436/548, 813

[56] References Cited

U.S. PATENT DOCUMENTS 4,752,569 6/1988 Terasaki et al. .................. 436/548

FOREIGN PATENT DOCUMENTS 0182495 5/1986 European Pat. Off. .
0182634 5/1986 European Pat. Off. .
WO8900169 1/1989 PCT Int'l Appl. .
WO8900190 1/1989 PCT Int'l Appl. .

OTHER PUBLICATIONS

K.-E. Arfors et al., "A Monoclonal Antibody to the Membrane Glycoprotein Complex CD18 Inhibits Polymorphonuclear Leukocyte Accumulation and Plasma Leakage In Vivo", *Blood*, 69, pp. 338-340 (1987).

A. Aruffo and B. Seed, "Molecular Cloning of a CD28 cDNA by a High Efficiency COS Cell Expression System", *Proc. Natl. Acad. Sci. USA*, 84, pp. 8573-8577 (1987).

S. Benchimol et al., "Carcinoembryonic Antigen, A Human Tumor Marker, Functions as an Intercellular Adhesion Molecule", *Cell*, 57, pp. 327-334 (1989).

M. P. Bevilacqua and M. A. Gimbrone, "Inducible Endothelial Functions in Inflammation and Coagulation", *Seminars in Thrombosis and Hemostasis*, 13, pp. 425-433 (1987).

M. P. Bevilacqua et al., "Interleukin 1 Acts on Cultured Human Vascular Endothelium to Increase the Adhesion of Polymorphonuclear Leukocytes, Monocytes, and Related Leukocyte Cell Lines", *J. Clin. Invest.*, 76, pp. 2003-2011 (1985) (Bevilacqua I).

M. P. Bevilacqua et al., "Endothelial-Dependent Mechanisms of Leukocyte Adhesion: Regulation by Interleukin-1 and Tumor Necrosis Factor", *Leukocyte Emigration and Its Sequelae* (S. Karger A.G., Switzerland, 1987), pp. 79-93 (1987) (Bevilacqua II).

M. P. Bevilacqua et al., "Identification of an Inducible Endothelial-Leukocyte Adhesion Molecule", *Proc. Natl. Acad. Sci. USA*, 84, pp. 9238-9242 (1987) (Bevilacqua III).

M. P. Bevilacqua et al., "Endothelial Leukocyte Adhesion Molecule 1: An Inducible Receptor for Neutrophils Related to Complement Regulatory Proteins and Lectins", *Science*, 243, pp. 1160-1165 (1989) (Bevilacqua IV).

M. Brenan and C. R. Parish, "Intracellular Fluorescent Labelling of Cells for Analysis of Lymphocyte Migration", *J. Immun. Meth.*, 74, pp. 31-38 (1984).

R. Cate et al., "Isolation of the Bovine and Human Genes for Mullerian Inhibiting Substance and Expression of the Human Gene in Animal Cells", *Cell*, 45, pp. 685-698 (1986).

R. S. Cotran and J. S. Pober, *Endothelial Cell Biology*, (Plenum Publishing Corporation, New York, 1988), pp. 335-347.

R. S. Cotran et al., "Induction and Detection of a Human Endothelial Activation Antigen In Vivo", *J. Exp. Med.*, 164, pp. 661-666 (1986).

N. Dana et al., "Mo1 Surface Glycoprotein: Structure, Function and Clinical Importance", *Pathol. Immunopathol. Res.*, 5, pp. 371-383 (1986).

(List continued on next page.)

Primary Examiner—David Saunders
Attorney, Agent, or Firm—James F. Haley, Jr.; Leon R. Yankwich; John R. Storella

[57] ABSTRACT

Monoclonal antibodies against CDX, a leukocyte cell surface molecule that is a ligand of ELAM 1, and methods for producing them. Monoclonal antibody SGB₃B₄ and monoclonal antibodies reactive to the same epitope. These monoclonal antibodies inhibit leukocyte-endothelial cell adhesion.

3 Claims, 6 Drawing Sheets

OTHER PUBLICATIONS

M. M. Davis, "Substractive cDNA Hybridization and the T-Cell Receptor Gene", *Handbook of Experimental Immunology In Four Volumes*, 4th ed. (Blackwell Scientific Publications, Oxford, England, 1986), pp. 76.1–76.13.

M. M. Davis et al., "Cell Type-Specific cDNA Probes and the Murine I Region: The Localization and Orientation of Ad", *Proc. Natl. Acad. Sci. USA*, 81, pp. 2194–2198 (1984).

J. R. Duguid et al., "Isolation of cDNAs of Scrapie-Modulated RNAs by Subtractive Hybridization of a cDNA Library", *Proc. Natl. Acad. Sci. USA*, 85, pp. 5738–5742 (1988).

A. P. Feinberg and B. Vogelstein, "A Technique for Radiolabeling DNA Restriction Endonuclease Fragments to High Specific Activity", *Anal. Biochem.*, 132, pp. 6–13 (1983).

A. P. Feinberg and B. Vogelstein, "A Technique for Radiolabeling DNA Restriction Endonuclease Fragments to High Specific Activity", *Anal. Biochem.*, 137, pp. 266–267 (1984) (Addendum).

R. A. Fisher et al., "HIV Infection Is Blocked In Vitro by Recombinant Soluble CD4", *Nature*, 331, pp. 76–78 (1988).

M. A. Gimbrone, Jr., "Culture of Vascular Endothelium", Prog. Hemostasis Thromb., 3, pp. 1–28 (1976).

M. A. Gimbrone, "Blood Vessels and the New Mediators of Inflammation", *Lab. Invest.*, 46, pp. 454–455 (1982).

W. Goding, ed., *Monoclonal Antibodies: Principles and Practice*, (Academic Press, New York, 1983), pp. 57–93.

V. Gubler and B. J. Hoffman, "A Simple and Very Efficient Method for Generating cDNA Libraries", *Gene*, 25, pp. 263–269.

J. M. Harlan, "Leukocyte-Endothelial Interactions," *Blood*, 65, pp. 513–525 (1985) (Harlan I).

J. M. Harlan, "Neurophil-Mediated Vascular Injury", *Acta Med. Scand.*, Suppl., 715, pp. 123–129 (1987) (Harlan II).

J. M. Harlan et al., *Leukocyte Emigration and Its Sequelae* (S. Karger AG, Switzerland, 1987), pp. 94–104.

S. M. Hedrick et al., "Isolation of cDNA Clones Encoding T Cell-Specific Membrane-Associated Proteins," *Nature*, 308, pp. 149–153 (1984).

B. Hirt, "Selective Extraction of Polyoma DNA from Infected Mouse Cell Cultures", *J. Mol. Biol.*, 26, pp. 365–369 (1967).

A. Hough and L. Sokoloff, "Pathology", Chap. 4, *Rheumatoid Arthritis* (Lippencott, Philadelphia, 1985), pp. 49–69.

T. Hunkapiller and L. Hood, "Diversity of the Immunoglobulin Gene Superfamily", *Adv. Immunol.*, 44, pp. 1–63 (1989).

K. Kurzinger et al., "A Novel Lymphocyte Function-Associated Antigen (LFA-1): Cellular Distribution, Quantitative Expression, and Structure", *J. Immunol.*, 127, pp. 596–602 (1981).

H. Lehrach et al., "RNA Molecular Weight Determinations by Gel Electrophoresis under Denaturing Conditions, a Critical Reexamination", *Biochem.*, 16, pp. 4743–4751 (1977).

H. L. Malech and J. I. Gallin, "Neutrophils in Human Diseases", *N. Eng. J. Med.*, 317, pp. 687–694 (1987).

T. Maniatis et al., *Molecular Cloning: A Laboratory Manual* (Cold Spring Harbor Laboratory, Cold Spring Harbor, New York, 1982).

J. L. Marx, "New Family of Adhesion Proteins Discovered", *Science*, 243, p. 1144 (1989).

A. Maxam and W. Gilbert, "Sequencing End-Labeled DNA with Base-Specific Chemical Cleavages", *Methods in Enzymol.*, 65, pp. 499–560 (1980).

R. Ross, "The Pathogenesis of Atherosclerosis—An Update", *N. Eng. J. Med*, 314, pp. 488–500 (1986).

R. M. Sandri-Goldin et al., "High Frequency Transfer of Cloned Herpes Simplex Virus Type I Sequences to Mammalian Cells by Protoplast Fusion", *Molec. and Cell Biol.*, 1, pp. 743–752 (1981).

T. D. Sargent, "Isolation of Differentially Expressed Genes", *Methods in Enzymol.*, 152, pp. 423–447 (1987).

B. Seed, "An LFA-3 cDNA Encodes a Phospholipid-Linked Membrane Protein Homologous to Its Receptor CD2", *Nature*, 329, pp. 840–842 (1987).

B. Seed and A. Aruffo, "Molecular Cloning of the CD2 Antigen, the T-Cell Erythrocyte Receptor, by a Rapid Immunoselection Procedure", *Proc. Natl. Acad. Sci. USA*, 84, pp. 3365–3369 (1987).

M. H. Siegelman et al., "Mouse Lymph Node Homing Receptor cDNA Clone Encodes a Glycoprotein Re- (List continued on next page.)

OTHER PUBLICATIONS vealing Tandem Interaction Domains", *Science*, 243, pp. 1165–1172 (1989).

Sims et al., "cDNA Expression Cloning of the IL-1 Receptor, a Member of the Immunoglobulin Superfamily", *Science*, 241, pp. 585–589 (1988).

D. Staunton et al., "Primary Structure of ICAM-1 Demonstrates Interaction Between Members of the Immunoglobulin and Integrin Supergene Families", *Cell*, 52, pp. 925–933 (1988).

R. F. Todd III et al., "The Anti-Inflammatory Properties of Monoclonal Anti-Mol (CD11B/CD18) Antibodies in Vitro and in Vivo," in *Structure and Function of Molecules Involved in Leukocyte Adhesion*, Rosethal et al., Eds., Springer—Verlag, New York (1989) in press.

J. Vane and R. Botting, "Inflammation and the Mechanism of Action of Anti-inflammatory Drugs", *FASEB J.*, 1, pp. 89–96 1989.

N. B. Vedder et al., "A Monoclonal Antibody to the Adherence-Promoting Leukocyte Glycoprotein, CD18, Reduces Organ Injury and Improves Survival from Hemorrhagic Shock and Resuscitation in Rabbits", *J. Clin. Invest.*, 81, pp. 939–944 (1988).

G. von Heijne, "A Method for Predicting Signal Sequence Cleavage Sites", *Nucl. Acids Res.*, 14, pp. 4693–4690 (1986).

M. E. Wheeler et al., "Cultured Human Endothelial Cells Stimulated with Cytokines or Endotoxin Produce an Inhibitor of Leukocyte Adhesion", *J. Clin. Invest.*, 82, pp. 1211–1218 (1988).

J. White and D. Littmann, "Viral Receptors of the Immunoglobulin Superfamily", *Cell*, 56, pp. 725–728 (1989).

A. Williams and A. N. Barclay, "The Immunoglobulin Superfamily—Domains for Cell Surface Recognition", *Ann. Rev. Immunol.*, 6, pp. 381–405 (1988).

L. J. Wysocki and V. L. Sato, "'Panning' for Lymphocytes: A Method for Cell Selection", *Proc. Natl. Acad. Sci. USA*, 75, pp. 2844–2848 (1978).

K. Yamasaki et al., "Cloning and Expression of the Human Interleukin-6 (BSF-2/IFNB2) Receptor", *Science*, 241, pp. 825–828 (1988).

R. A. Young and R. W. Davis, "Efficient Isolation of Genes by Using Antibody Probes", *Proc. Natl. Acad. Sci. USA*, 80, pp. 1194–1198 (1983) (Young I).

R. A. Young and R. W. Davis, "Yeast RNA Polymerase II Genes: Isolation with Antibody Probes", *Science*, 222, pp. 778–782 (1984) (Young II).

G. Walz et al, *Science*, 250, 1130–1132, 1990.

T. A. Springer et al, *Nature*, 349, 196–197, 1991.

Goelz et al, *Cell*, 63, 1349–1356, 1990.

FIG. 1A

```
  1  TTCACATCAAAACTCCTATACTGACCTGAGACAGAGGCAGCAGTGATACC   50

51  CACCTGAGAGATCCTGTGTTTGAACAACTGCTTCCCAAAACGGAAAGTAT  100

101  TTCAAGCCTAAACCTTTGGGTGAAAAGAACTCTTGAAGTCATGATTGCTT  150
                                              MetIleAlaS

151  CACAGTTTCTCTCAGCTCTCACTTTGGTGCTTCTCATTAAAGAGAGTGGA  200
     erGlnPheLeuSerAlaLeuThrLeuValLeuLeuIleLysGluSerGly

201  GCCTGGTCTTACAACACCTCCACGGAAGCTATGACTTATGATGAGGCCAG  250
     AlaTrpSerTyrAsnThrSerThrGluAlaMetThrTyrAspGluAlaSe

251  TGCTTATTGTCAGCAAAGGTACACACACCTGGTTGCAATTCAAAACAAAG  300
     rAlaTyrCysGlnGlnArgTyrThrHisLeuValAlaIleGlnAsnLysG

301  AAGAGATTGAGTACCTAAACTCCATATTGAGCTATTCACCAAGTTATTAC  350
     luGluIleGluTyrLeuAsnSerIleLeuSerTyrSerProSerTyrTyr

351  TGGATTGGAATCAGAAAAGTCAACAATGTGTGGGTCTGGGTAGGAACCCA  400
     TrpIleGlyIleArgLysValAsnAsnValTrpValTrpValGlyThrGl

401  GAAACCTCTGACAGAAGAAGCCAAGAACTGGGCTCCAGGTGAACCCAACA  450
     nLysProLeuThrGluGluAlaLysAsnTrpAlaProGlyGluProAsnA

451  ATAGGCAAAAGATGAGGACTGCGTGGAGATCTACATCAAGAGAGAAAAA   500
     snArgGlnLysAspGluAspCysValGluIleTyrIleLysArgGluLys

501  GATGTGGGCATGTGGAATGATGAGAGGTGCAGCAAGAAGAAGCTTGCCCT  550
     AspValGlyMetTrpAsnAspGluArgCysSerLysLysLysLeuAlaLe

551  ATGCTACACAGCTGCCTGTACCAATACATCCTGCAGTGGCCACGGTGAAT  600
     uCysTyrThrAlaAlaCysThrAsnThrSerCysSerGlyHisGlyGluC

601  GTGTAGAGACCATCAATAATTACACTTGCAAGTGTGACCCTGGCTTCAGT  650
     ysValGluThrIleAsnAsnTyrThrCysLysCysAspProGlyPheSer

651  GGACTCAAGTGTGAGCAAATTGTGAACTGTACAGCCCTGGAATCCCCTGA  700
     GlyLeuLysCysGluGlnIleValAsnCysThrAlaLeuGluSerProGl

701  GCATGGAAGCCTGGTTTGCAGTCACCCACTGGGAAACTTCAGCTACAATT  750
     uHisGlySerLeuValCysSerHisProLeuGlyAsnPheSerTyrAsnS

751  CTTCCTGCTCTATCAGCTGTGATAGGGGTTACCTGCCAAGCAGCATGGAG  800
     erSerCysSerIleSerCysAspArgGlyTyrLeuProSerSerMetGlu
```

FIG. 1B

```
 801  ACCATGCAGTGTATGTCCTCTGGAGAATGGAGTGCTCCTATTCCAGCCTG   850
      ThrMetGlnCysMetSerSerGlyGluTrpSerAlaProIleProAlaCy

851  CAATGTGGTTGAGTGTGATGCTGTGACAAATCCAGCCAATGGGTTCGTGG   900
      sAsnValValGluCysAspAlaValThrAsnProAlaAsnGlyPheValG

901  AATGTTTCCAAAACCCTGGAAGCTTCCCATGGAACACAACCTGTACATTT   950
      luCysPheGlnAsnProGlySerPheProTrpAsnThrThrCysThrPhe

951  GACTGTGAAGAAGGATTTGAACTAATGGGAGCCCAGAGCCTTCAGTGTAC  1000
      AspCysGluGluGlyPheGluLeuMetGlyAlaGlnSerLeuGlnCysTh

1001  CTCATCTGGGAATTGGGACAACGAGAAGCCAACGTGTAAAGCTGTGACAT  1050
      rSerSerGlyAsnTrpAspAsnGluLysProThrCysLysAlaValThrC

1051  GCAGGGCCGTCCGCCAGCCTCAGAATGGCTCTGTGAGGTGCAGCCATTCC  1100
      ysArgAlaValArgGlnProGlnAsnGlySerValArgCysSerHisSer

1101  CCTGCTGGAGAGTTCACCTTCAAATCATCCTGCAACTTCACCTGTGAGGA  1150
      ProAlaGlyGluPheThrPheLysSerSerCysAsnPheThrCysGluGl

1151  AGGCTTCATGTTGCAGGGACCAGCCCAGGTTGAATGCACCACTCAAGGGC  1200
      uGlyPheMetLeuGlnGlyProAlaGlnValGluCysThrThrGlnGlyG

1201  AGTGGACACAGCAAATCCCAGTTTGTGAAGCTTTCCAGTGCACAGCCTTG  1250
      lnTrpThrGlnGlnIleProValCysGluAlaPheGlnCysThrAlaLeu

1251  TCCAACCCCGAGCGAGGCTACATGAATTGTCTTCCTAGTGCTTCTGGCAG  1300
      SerAsnProGluArgGlyTyrMetAsnCysLeuProSerAlaSerGlySe

1301  TTTCCGTTATGGGTCCAGCTGTGAGTTCTCCTGTGAGCAGGGTTTTGTGT  1350
      rPheArgTyrGlySerSerCysGluPheSerCysGluGlnGlyPheValL

1351  TGAAGGGATCCAAAAGGCTCCAATGTGGCCCCACAGGGGAGTGGGACAAC  1400
      euLysGlySerLysArgLeuGlnCysGlyProThrGlyGluTrpAspAsn

1401  GAGAAGCCCACATGTGAAGCTGTGAGATGCGATGCTGTCCACCAGCCCCC  1450
      GluLysProThrCysGluAlaValArgCysAspAlaValHisGlnProPr

1451  GAAGGGTTTGGTGAGGTGTGCTCATTCCCCTATTGGAGAATTCACCTACA  1500
      oLysGlyLeuValArgCysAlaHisSerProIleGlyGluPheThrTyrL

1501  AGTCCTCTTGTGCCTTCAGCTGTGAGGAGGGATTTGAATTACATGGATCA  1550
      ysSerSerCysAlaPheSerCysGluGluGlyPheGluLeuHisGlySer

1551  ACTCAACTTGAGTGCACATCTCAGGGACAATGGACAGAAGAGGTTCCTTC  1600
      ThrGlnLeuGluCysThrSerGlnGlyGlnTrpThrGluGluValProSe
```

FIG. IC

```
1601  CTGCCAAGTGGTAAAATGTTCAAGCCTGGCAGTTCCGGGAAAGATCAACA  1650
      rCysGlnValValLysCysSerSerLeuAlaValProGlyLysIleAsnM
1651  TGAGCTGCAGTGGGGAGCCCGTGTTTGGCACTGTGTGCAAGTTCGCCTGT  1700
      etSerCysSerGlyGluProValPheGlyThrValCysLysPheAlaCys
1701  CCTGAAGGATGGACGCTCAATGGCTCTGCAGCTCGGACATGTGGAGCCAC  1750
      ProGluGlyTrpThrLeuAsnGlySerAlaAlaArgThrCysGlyAlaTh
1751  AGGACACTGGTCTGGCCTGCTACCTACCTGTGAAGCTCCCACTGAGTCCA  1800
      rGlyHisTrpSerGlyLeuLeuProThrCysGluAlaProThrGluSerA
1801  ACATTCCCTTGGTAGCTGGACTTTCTGCTGCTGGACTCTCCCTCCTGACA  1850
      snIleProLeuValAlaGlyLeuSerAlaAlaGlyLeuSerLeuLeuThr
1851  TTAGCACCATTTCTCCTCTGGCTTCGGAAATGCTTACGGAAAGCAAAGAA  1900
      LeuAlaProPheLeuLeuTrpLeuArgLysCysLeuArgLysAlaLysLy
1901  ATTTGTTCCTGCCAGCAGCTGCCAAAGCCTTGAATCAGATGGAAGCTACC  1950
      sPheValProAlaSerSerCysGlnSerLeuGluSerAspGlySerTyrG
1951  AAAAGCCTTCTTACATCCTTTAAGTTCAAAAGAATCAGAAACAGGTGCAT  2000
      lnLysProSerTyrIleLeu
2001  CTGGGGAACTAGAGGGATACACTGAAGTTAACAGAGACAGATAACTCTCC  2050
2051  TCGGGTCTCTGGCCCTTCTTGCCTACTATGCCAGATGCCTTTATGGCTGA  2100
2101  AACCGCAACACCCATCACCACTTCAATAGATCAAAGTCCAGCAGGCAAGG  2150
2151  ACGGCCTTCAACTGAAAAGACTCAGTGTTCCCTTTCCTACTCTCAGGATC  2200
2201  AAGAAAGTGTTGGCTAATGAAGGGAAAGGATATTTTCTTCCAAGCAAAGG  2250
2251  TGAAGAGACCAAGACTCTGAAATCTCAGAATTCCTTTTCTAACTCTCCCT  2300
2301  TGCTCGCTGTAAAATCTTGGCACAGAAACACAATATTTTGTGGCTTTCTT  2350
2351  TCTTTTGCCCTTCACAGTGTTTCGACAGCTGATTACACAGTTGCTGTCAT  2400
2401  AAGAATGAATAATAATTATCCAGAGTTTAGAGGAAAAAAATGACTAAAAA  2450
2451  TATTATAACTTAAAAAATGACAGATGTTGAATGCCCACAGGCAAATGCAT  2500
2501  GGAGGGTTGTTAATGGTGCAAATCCTACTGAATGCTCTGTGCGAGGGTTA  2550
2551  CTATGCACAATTTAATCACTTTCATCCCTATGGGATTCAGTGCTTCTTAA  2600
```

FIG. 1D

```
2601  AGAGTTCTTAAGGATTGTGATATTTTTACTTGCATTGAATATATTATAAT  2650
2651  CTTCCATACTTCTTCATTCAATACAAGTGTGGTAGGGACTTAAAAAACTT  2700
2701  GTAAATGCTGTCAACTATGATATGGTAAAAGTTACTTATTCTAGATTACC  2750
2751  CCCTCATTGTTTATTAACAAATTATGTTACATCTGTTTTAAATTTATTTC  2800
2801  AAAAAGGGAAACTATTGTCCCCTAGCAAGGCATGATGTTAACCAGAATAA  2850
2851  AGTTCTGAGTGTTTTTACTACAGTTGTTTTTGAAAACATGGTAGAATTG   2900
2901  GAGAGTAAAAACTGAATGGAAGGTTTGTATATTGTCAGATATTTTTTCAG  2950
2951  AAATATGTGGTTTCCACGATGAAAAACTTCCATGAGGCCAAACGTTTTGA  3000
3001  ACTAATAAAAGCATAAATGCAAACACACAAAGGTATAATTTTATGAATGT  3050
3051  CTTTGTTGGAAAAGAATACAGAAAGATGGATGTGCTTTGCATTCCTACAA  3100
3101  AGATGTTTGTCAGATATGATATGTAAACATAATTCTTGTATATTATGGAA  3150
3151  GATTTTAAATTCACAATAGAAACTCACCATGTAAAAGAGTCATCTGGTAG  3200
3201  ATTTTTAACGAATGAAGATGTCTAATAGTTATTCCCTATTTGTTTTCTTC  3250
3251  TGTATGTTAGGGTGCTCTGGAAGAGAGGAATGCCTGTGTGAGCAAGCATT  3300
3301  TATGTTTATTTATAAGCAGATTTAACAATTCCAAAGGAATCTCCAGTTTT  3350
3351  CAGTTGATCACTGGCAATGAAAAATTCTCAGTCAGTAATTGCCAAAGCTG  3400
3401  CTCTAGCCTTGAGGAGTGTGAGAATCAAAACTCTCCTACACTTCCATTAA  3450
3451  CTTAGCATGTGTTGAAAAAAAGTTTCAGAGAAGTTCTGGCTGAACACTG   3500
3501  GCAACAACAAAGCCAACAGTCAAAACAGAGATGTGATAAGGATCAGAACA  3550
3551  GCAGAGGTTCTTTTAAAGGGGCAGAAAAACTCTGGGAAATAAGAGAGAAC  3600
3601  AACTACTGTGATCAGGCTATGTATGGAATACAGTGTTATTTTCTTTGAAA  3650
3651  TTGTTTAAGTGTTGTAAATATTTATGTAAACTGCATTAGAAATTAGCTGT  3700
3701  GTGAAATACCAGTGTGGTTTGTGTTTGAGTTTTATTGAGAATTTTAAATT  3750
3751  ATAACTTAAAATATTTTATAATTTTTAAAGTATATATTTATTTAAGCTTA  3800
```

FIG. IE

3801 TGTCAGACCTATTTGACATAACACTATAAAGGTTGACAATAAATGTGCTT 3850

3851 ATGTTTAAAAAAA 3863

FIG. 2

```
         N                                                    N                                         N
      D BEsSS                                              sEEN                                      D sS BES
      s gapaf                                              paao                                      s pa gaf
      a leBcl                                              Regt                                      a Bc lel
      1 11221                                              1111                                      1 22 111
                                                            X
                                                            h
                                                            o
                                                            2
N
h
e
l   GctAGCCGGCCTCCGGGCCAGTCCAACCACCAATCTCAAAGCATAGGCGACACATGGGCCCAAAACGATCAGCAGATCCTCACATCCCAATCCGAGGCCGGTGGCCGC
401 ----------+---------+---------+---------+---------+---------+---------+---------+---------+---------+ 510
    CgaTCGGCCGGAGGCCGGTCAGGTTGGTGGTTAGAGTTTGTATCCGCTGTAGCCGGCCGTTTGTGTAGTCGTCTAGGAGTGTAGGGTTAGGCTCCGGCCACCGGCG
```

MONOCLONAL ANTIBODIES AGAINST CDX

TECHNICAL FIELD OF INVENTION

This invention relates to molecules involved in adhesion of leukocytes to endothelial cells during inflammation. More particularly, it relates to endothelial cell-leukocyte adhesion molecules (ELAMs), which are expressed on endothelial cells, and molecules involved in leukocyte adhesion to endothelial cells (MILAs) which are expressed on leukocytes. Specifically, we disclose here the ELAM, ELAM 1, and the MILA, CDX. This invention also relates to DNA sequences which code on expression for ELAMs and MILAs and to antibodies against MILAs. This invention also relates to methods of using ELAMs and MILAs, for example in developing diagnostic agents and therapeutic agents which inhibit leukocyte adhesion to endothelial cells.

BACKGROUND OF THE INVENTION

Inflammation is the response of vascularized tissues to infection or injury. Clinically it is accompanied by four classic signs: redness, heat, pain, and swelling. Its course may be acute or chronic.

At the cellular level, inflammation involves the adhesion of leukocytes (white blood cells) to the endothelial wall of blood vessels and their infiltration into the surrounding tissues. (Harlan, J. M., "Leukocyte-Endothelial Interactions," *Blood,* 65, pp. 513-25 (1985).) Acute inflammation is characterized by the adhesion and infiltration of polymorphonuclear leukocytes (PMNs). (Harlan, J. M., "Neutrophil-Mediated Vascular Injury," *Acta Med. Scand. Suppl.,* 715, pp. 123-29 (1987) and Malech, H. L., and Gallin, J. I., "Neutrophils in Human Disease," *N. Eng. J. Med.,* 317, 687-94 (1987).) PMN accumulation in the tissues reaches its peak between two-and-a-half to four hours after an inflammatory stimulus and ceases by about twenty-eight hours. (Bevilaqua, M. P., and M. A. Gimbrone, "Inducible Endothelial Functions in Inflammation and Coagulation," *Seminars in Thrombasis and Hemostasis,* 13, pp. 425-33 (1987).) In contrast, chronic inflammation is characterized by the adhesion and infiltration of other leukocytes, especially monocytes and lymphocytes.

In normal inflammation, the infiltrating leukocytes phagocytose invading organisms or dead cells, and play a role in tissue repair. However, in pathologic inflammation, infiltrating leukocytes can cause serious and sometimes deadly damage. Rheumatoid arthritis, atherosclerosis, and allograft rejection are examples of chronic inflammatory diseases in which mononuclear leukocytes infiltate the tissues and cause damage. (Ross, R., "The Pathogenesis of Atherosclerosis—An Update," *N. Eng. J. Med.,* 314, pp. 123-29 (1986). Multiple organ failure syndrome, adult respiratory distress syndrome (ARDS), and ischemic reperfusion injury are acute inflammations in which infiltrating PMNs cause the damage. (Harlan, *Acta Med. Scand., Suppl.,* supra; and *Malech and Gallin,* supra.) In multiple organ failure syndrome, which can occur after shock such as that associated with severe burns, PMN-mediated damage exacerbates the injury. In ARDS, PMNs cause the lungs to fill with fluid and the victim may drown. In ischemic reperfusion injury, which occurs when tissue cut-off from the supply of blood is suddenly perfused with blood (for example after heart attack, stroke, or limb re-attachment), PMN adhesion causes serious tissue damage. (Harlan, *Acta. Med. Scand., Suppl.,* supra.)

Recognizing that leukocyte infiltration is the cause of much inflammation-related pathology and that leukocyte adhesion is the first step in infiltration, investigators have recently focused attention on the mechanism of leukocyte binding to the endothelial wall. Studies show that binding is mediated by cell-surface molecules on both endothelial cells and leukocytes which act as receptor and ligand. (Harlan, J. M. et al., "The Role of Neutrophil Membrane Proteins in Neutrophil Emigration," in *Leukocyte Emigration and Its Sequelae,* H. Movat, ed., Karger, Basel, pp. 94-104 (1987); Dana, N., et al., "Mol Surface Glycoprotein: Structure, Function, and Clinical Importance." *Pathol. Immunopathol. Res.* 5, p. 371 (1986); Bevilaqua, M. P., et al., "Endothelial Dependent Mechanisms of Leukocyte Adhesion: Regulation by Interleukin 1 and Tumor Necrosis Factor," in *Leukocyte Emigration and Its Sequelae,* H. Movat, ed., Karger, Basel, pp. 79-93 (1987).)

In leukocyte-mediated adhesion, certain inflammatory agents act on the leukocyte, making it hyperadhesive for endothelium. These inflammatory agents include leukotriene-B4 (LTB4), complement factor 5a (C5a), and formyl-methionyl-leucyl-phenylalanine (FMLP). These agents activate a group of proteins called LeuCAMs. The LeuCAMs are dimers of the CD11 and CD18 proteins. One of the LeuCAMs, CD11a/CD18, (also called LFA-1) binds to a receptor on endothelial cells called ICAM1 (immune cell adhesion molecule). (Harlan, supra, and Dana et al., supra.) Investigators have shown that monoclonal antibodies (Moabs) to LeuCAMs inhibit PMN adhesion to endothelium both in vitro and in vivo. (Arfors, K-E., et al., "A Monoclonal Antibody to the Membrane Glycoprotein Complex CD18 Inhibits Polymorphonuclear Leukocyte Accumulation and Plasma Leakage In Vivo." *Blood,* 69, 338-40 (1986); Vedder, N. B., et al., "A Monoclonal Antibody to the Adherence-Promoting Leukocyte Glycoprotein, CD18, Reduces Organ Injury and Improves Survival from Hemorrhagic Shock and Resuscitation in Rabbits," *J. Clin. Invest.,* 81, pp. 939-44 (1988); and Todd, R. F. III, et al., "The Anti-Inflammatory Properties of Monoclonal Anti-Mol (CD11B/CD18) Antibodies in Vitro and in Vivo," in *Structure and Function of Molecules Involved in Leukocyte Adhesion,* Rosenthal, A. S., et al., Eds., Springer-Verlag, New York (1989), in press.)

In endothelial cell-mediated adhesion, certain inflammatory agents act directly on endothelial cells to substantially augment leukocyte adhesion. These agents include the cytokines interleukin-1 (IL-1), lymphotoxin (LT) and tumor necrosis factor (TNF), as well as the bacterial endotoxin, lipopolysaccharide (LPS). For example, IL-1 stimulates adhesion of PMNs, monocytes, and the related cell lines HL-60 (PMN-like) and U937 (monocyte-like) to human endothelial cell monolayers. The action is both time-dependent and protein-synthesis dependent. (Bevilaqua et al., in *Leukocyte Emigration and Its Sequelae,* supra; Bevilaqua et al., "Identification of an Inducible Endothelial-Leukocyte Adhesion Molecule," *Proc. Natl. Acad. Sci., USA,* 84, pp. 9238-42 (1987); Bevilaqua, M. P., et al., "Interleukin 1 Acts on Cultured Human Vascular Endothelium to Increase the Adhesion of Polymorphonuclear Leukocytes, Monocytes, and Related Cell Lines," *J. Clin. Invest.,* 76, pp. 2003-11 (1985).)

Current evidence indicates that these agents activate a group of molecules on the endothelial surface called ELAMs (endothelial cell-leukocyte adhesion molecules). Investigators have identified one of these molecules and named it ELAM1. (Bevilaqua et al., *Proc. Natl. Acad. Sci., U.S.A.*, supra.) ELAM1 is a 116 kD cell-surface glycoprotein which is induced in vitro on human umbilical vein endothelial cells (HUVECs) by cytokines but which is absent from unstimulated cells. Importantly, the presence of ELAM1 on the cell surface follows the natural course of acute inflammation, appearing a few hours after stimulation and gradually dissipating within a day. (Bevilaqua et al., *Proc. Natl. Acad. Sci., USA.*, supra.)

ELAM1 is also present in vivo. Immunohistologic studies show that it exists at sites of acute, but not chronic, inflammation, and is absent from the non-inflamed vessel wall (Cotran, R. S., et al., "Induction and Detection of a Human Endothelial Activation Antigen In Vivo," *J. Exp. Med.*, 164, 661–666 (1986) and Cotran, R. S., and J. S. Pober, "Endothelial Activation: Its Role in Inflammatory and Immune Reactions," in *Endothelial Cell Biology*, Simionescu and Simionescu, Eds., pp. 335–47, Plenum Press (1988)). Therefore, ELAM1 appears to be a major mediator of PMN and monocyte adhesion to the inflamed vascular wall in vivo.

There is reason to believe that other ELAMs exist. Although inflammatory agents induce binding of PMNs, monocytes, and lymphocytes, Moabs against ELAM1 inhibit only the binding of PMNs and related cells. (Bevilaqua and Gimbrone, *Seminars in Thrombosis and Hemostasis*, supra.) Furthermore, lymphocytes and monocytes accumulate in the tissues after twenty-four hours, when ELAM1 expression has returned to basal levels. Therefore, other ELAMs probably mediate binding of these leukocytes. (See, Bevilaqua et al., *Proc. Natl. Acad. Sci., U.S.A.*, supra.) ELAMs accordingly may be regarded as a family of molecules that are induced in endothelial cells at sites of acute inflammation and selectively mediate binding of specific leukocyte classes to the endothelial wall en route to leukocyte infiltration.

The adhesion of leukocytes to cells expressing ELAM1 suggests the existence on leukocytes of an ELAM1 ligand. We report here the isolation of a molecule involved in leukocyte adhesion to endothelial cells (MILA) which may prove to be an ELAM ligand. The molecule, designated CDX, was isolated from HL-60 cells. Monoclonal antibodies which recognize CDX inhibit the binding of PMNs and HL-60 cells to ELAM-expressing cells. Furthermore, CDX is present on leukocyte cell types known to adhere to ELAM1 and is absent from leukocyte cell types and other cell types which do not adhere to ELAM1. Thus, CDX is a molecule expressed on certain leukocytes which plays an important role in ELAM1-mediated leukocyte-endothelial cell adhesion.

Because leukocyte adhesion to the vascular wall is the first step in PMN-mediated tissue damage during inflammation, therapies directed to preventing this step are attractive. Clinicians are already testing, with some success, therapies based on inhibiting leukocyte-mediated adhesion. One approach involves Moab binding to the leukocyte cell-surface complex, CD11/CD18, to inhibit PMN adhesion. (Arfors et al., supra; Vedder et al., supra; and Todd et al., supra.)

We believe that alternative therapies for preventing leukocyte adhesion, based on endothelial cell-mediated binding, and on ELAMs and MILAs (including ELAM ligands), in particular, are more promising. The ELAM system is particularly appealing for two reasons: First, because ELAM expression is induced rather than constitutive, ELAMs exist only at sites of inflammation and are limited in number. This means that adhesion inhibitors need act only locally and, consequently, would be effective at lower doses than inhibitors directed to constitutively expressed molecules. Second, ELAM binding is selective for different leukocyte classes—ELAM1 binds PMNs, especially. Therefore, these therapies would be specific for PMN-mediated damage and would not affect the trafficking of other leukocytes. Furthermore, for the above reasons, such therapies may prove to be cheaper and less toxic.

ELAM-based approaches to therapy require, as starting materials, both ELAM and MILA in highly purified form, free of normally associated animal proteins. There is also a need for methods to produce these molecules. Recombinant DNA technology, when applied to the problem, provides powerful means to develop such methods, e.g., by isolating DNA sequences which code on expression for particular molecules, and by constructing recombinant DNA molecules and expression vehicles for their production.

SUMMARY OF THE INVENTION

It is the principal object of this invention to provide new means to study, diagnose, prevent, and treat inflammation. More particularly, it is an object of this invention to provide molecules involved in leukocyte binding to endothelial cells and to isolate other molecules which are themselves useful in inhibiting the endothelial-cell binding to leukocytes.

This invention provides for DNA sequences which code on expression for endothelial cell-leukocyte adhesion molecules (ELAMs), the molecules on endothelial cells which mediate binding to PMNs, recombinant DNA molecules containing these DNA sequences, unicellular hosts transformed with these DNA molecules, processes for producing ELAMs, and ELAMs essentially free of normally associated animal proteins. It also provides for antibody preparations reactive for ELAMs.

This invention also provides for DNA sequences which code on expression for molecules involved in leukocyte adhesion to endothelial cells (MILAs). MILAs will include leukocyte surface molecules which bind directly to ELAMs, i.e., ELAM ligands. Monoclonal antibodies recognizing ELAM ligands can inhibit ELAM/ELAM ligand binding directly. MILAs will also include leukocyte surface molecules which are involved indirectly in adhesion, for example molecules which can inhibit ELAM/ELAM ligand binding by interacting with a third molecule, such as a monoclonal antibody. Such molecules may act, for example, by changing the surface conformation of an ELAM ligand so that its affinity for the ELAM is reduced.

We have identified a MILA, referred to herein as CDX, which is a 175 kD leukocyte surface protein. Exposing CDX to monoclonal antibodies raised against it inhibits leukocyte-endothelial cell adhesion.

This invention also provides for recombinant DNA molecules containing these DNA sequences and unicellular hosts transformed with them. It also provides for MILAs essentially free of normally associated animal proteins and methods for producing MILAs. Also, it provides for monoclonal antibodies which recognize MILAs in general and CDX in particular.

This invention further provides for methods for inhibiting PMN binding to endothelial cells involving using ELAM, MILA including ELAM ligand, or portions of those molecules to block receptors or ligands. It also relates to methods for identifying molecular inhibitors of binding by screening molecules for their ability to inhibit binding of ELAM to ELAM ligand.

BRIEF DESCRIPTION OF THE DRAWINGS

FIGS. 1A-1E depict the composite ELAM1 cDNA sequence and deduced amino acid sequence derived from the DNA sequence of ELAM pCDM8 clone 6, pSQ148 and pSQ149. The nucleotides are numbered from 1 to 3863. FIG. 1A depicts nucleotides 1 to 800. FIG. 1B depicts nucleotides 801 to 1600. FIG. 1C depicts ncleotides 1601 to 2600. FIG. 1D depicts neucleotides 2601 to 3800. FIG. 1E depicts nucleotides 3801 to 3863. Throughout this application we refer to the coding DNA sequence of these Figures as the CNA sequence for ELAM1. We also refer to the molecule comprising the amino acid sequence depicted in these Figures as ELAM1.

FIG. 2 depicts the DNA sequence of the synthetic polylinker of pNN11.

DETAILED DESCRIPTION OF THE INVENTION

In accordance with this detailed description, the following definitions apply:

Expression control sequence—A DNA sequence which controls and regulates the transcription and translation of another DNA sequence.

Operatively linked—A DNA sequence is operatively linked to an expression control sequence when the expression control sequence controls and regulates the transcription and translation of that DNA sequence. The term "operatively linked" includes having an appropriate start signal (e.g., ATG) in front of the DNA sequence to be expressed and maintaining the correct reading frame to permit expression of the DNA sequence under the control of the expression control sequence and production of the desired product encoded by the DNA sequence. If a gene that one desires to insert into a recombinant DNA molecule does not contain an appropriate start signal, such a start signal can be inserted in front of the gene.

Antibody—An immunoglobulin molecule or fragment thereof, such as Fab or F(ab')$_2$. An antibody preparation is reactive for an antigen when a substantial portion of the individual immunoglobulin molecules recognize the antigen. An antibody preparation is nonreactive for an antigen when only an insubstantial portion of the individual immunoglobulin molecules recognize the antigen.

Standard hybridization conditions—salt and temperature conditions substantially equivalent to 5 x SSC and 65° C. for both hybridization and wash.

DNA sequences—The DNA sequences of this invention refer to DNA sequences prepared or isolated using recombinant DNA techniques. These include cDNA sequences, DNA sequences isolated from their native genome, and synthetic DNA sequences. The term as used in the claims is not intended to include naturally occurring DNA sequences as they exist in Nature.

Our technical goals in this invention are to isolate and sequence a cDNA from an ELAM mRNA, to express ELAM molecules in an appropriate host, to isolate a MILA, and to isolate and express a DNA sequence for a MILA and an ELAM ligand in particular. It should be understood that expression may involve post-translational modifications effected by the host cell. For example, in mammalian cells expression might include, among other things, glycosylation of a polypeptide or cleavage of a signal sequence to produce a "mature" polypeptide. Accordingly, the present invention contemplates glycosylated and unglycosylated polypeptides, and also mature polypeptides and polypeptides retaining a signal peptide.

ELAMs are expressed on the surface of endothelial cells only during inflammation. We utilized this phenomenon to isolate an ELAM cDNA. We call the polypeptide product encoded by our isolate ELAM1. The first step involved in the isolation was selection of cells which differentially expressed the molecule. We chose human umbilical vein endothelial cells because they produce ELAMs when induced by the inflammatory cytokine IL-1$\beta$. However, the practitioner is not limited to this cell type, or even to human cells in particular. Other mammalian cells, e.g., baboon endothelial cells, are also known to produce ELAMs. (Cotran and Pober, supra.)

The next step is to isolate mRNA from cells expressing ELAM1, and to create a cDNA library from it. Many methods are known for isolating mRNA and for producing cDNA from it. (See, e.g., Gubler, U., and R. J. Hoffman, "A Simple and Very Effective Method for Generating cDNA Libraries," *Gene*, 25, pp. 263-69 (1983) and Maniatis., T., *Molecular Cloning: A Laboratory Manual*, Cold Spring Harbor (1982).)

One then inserts the cDNA into an appropriate vector. We chose the eukaryotic expression vector pCDM8, described by Brian Seed. (Seed, B. "An LFA-3 cDNA Encodes a Phospholipid-Linked Membrane Protein Homologous to Its Receptor CDs," *Nature*, 329, pp. 840-42 (1987).) This plasmid has several advantages including a high copy number in *E.coli*, a eukaryotic promoter, and high level of expression in transient expression systems such as COS 7. However, several other vector systems are available. (Cate, R., et al., "Isolation of the Bovine and Human Gene for Mullerian Inhibiting Substance and Expression of the Human Gene in Animal Cells," *Cell*, 45, pp. 685-98 (1986).)

Once one has constructed a cDNA library, the next step is to isolate from it clones containing ELAM DNA sequences. There are currently many ways to isolate cDNA for a differentially expressed mRNA. These include first, plus/minus screening cDNA libraries; and third, screening with subtractive probes. (Davis, M. M., "Subtractive cDNA Hybridization and the T-cell Receptor Genes,", *Handbook of Experimental Immunology*, Weir, Ed., Vol. 2, Chap. 76, 76.1-76.13. (1986); Sargent, T. D., "Isolation of Differentially Expressed Genes," *Methods in Enzymology*, 152, pp. 423-47 (198 ): Davis, M. M. et al., "Cell Type-Specific cDNA Probes and the Murine I Region: The Localization and Orientation of A$_a$$^d$," *Proc. Natl. Acad. Sci., U.S.A.*, 81, pp. (1984); Hendrick, S. M. et al., "Isolation of cDNA Clones Encoding T Cell-Specific Membrane-Associated Proteins," *Nature*, 308, pp. 149-53 (1984); Duguid, J. R., et al., "Isolation of cDNAs of Scrapie-Modulated RNAs by Subtractive Hybridization of a cDNA Library," *Proc. Natl. Acad. Sci., USA*, 85, pp. 5738–42 (1988).) We chose the third technique, screening with subtractive cDNA probes, and produced a cDNA sublibrary enriched for ELAM sequences.

As we will describe in more detail below, we produced a subtractive cDNA probe specific for mRNA produced by induced, but not uninduced cells. Then we probed the cDNA library with the subtracted cDNA probe using techniques well known to the art. This enabled us to isolate clones forming a sublibrary enriched for ELAM sequences.

At this point we used two techniques to identify which clones contained cDNA for ELAM sequences. In a first method, we tested clones for expression of ELAM activity in an appropriate eukaryotic expression system. One can use a variety of direct expression techniques, including antibody screening of fusion proteins encoded by cDNA cloned in λGT11 (Young, R. A., and R. W. Davis, *Proc. Natl. Acad. Sci., USA*, 80, pp. 1194–98 (1983) and Young, R. A., and R. W. Davis, *Science*, 222, pp. 778–82 (1984).); or activity assay of oocyte-conditioned media after injection of mRNA from cloned cDNA, or from plasmid or phage carrying SP6/T7 promoters. Alternatively, one can make libraries in plasmid, phage, and cosmid vectors containing a variety of promoter, selection and replication elements. One can transfect the library into animal cells for transient or stable expression. Transfection can be accomplished by a variety of methods. For transient expression, investigators have used spheroplast fusion, DEAE dextran, and electroporation. For stable expression they have used calcium phosphate, spheroplast fusion, and electroporation. We used COS 7 cells, a transient expression system, transfected by spheroplast fusion. (Aruffo, A., and B. Seed, "Molecular Cloning of a CD28 cDNA by a High Efficiency COS Cell Expression System," *Proc. Natl. Acad. Sci., USA*, 84, pp. 8573–77 (1987).)

Until recently, identification of cloned molecules by direct expression has required sensitive assays and has been restricted to lymphokines. However, cDNA cloning of single-chain cell-surface molecules in efficient transient expression vectors (see, e.g., Seed, B. and A. Aruffo, "Molecular Cloning of the CD2 Antigen, the T-Cell Erythrocyte Receptor, by a Rapid Immunoselection Procedure," *Proc. Natl. Acad. Sci., U.S.A.*, 84, pp. 3365–69 (1987); Seed, B., "An LFA-3 cDNA Encodes a Phospholipid-Linked Membrane Protein Homologous to Its Receptor CD2," *Nature*, 329, pp. 840–42 (1987)), either by adaption of antibody "panning" technology (Wysocki, L. J. and V. L. Sato, *Proc. Natl. Acad. Sci., U.S.A.*, 75, pp. 2844–48 (1978)), or by identification of functional molecules by FACS (Yamasaki, K. et al., *Science*, 241, pp. 825–27 (1988)), has expanded the range of cloned molecules that one can identify by direct expression.

We have extended this technology by using an adhesion assay in which an appropriate cell type, expressing the ligand for the cloned molecule, is used to identify that molecule.

We detected expression by testing the ability of transfected cells to bind the human neutrophil-like cell line, HL-60. (Bevilaqua, M. P., et al., *J. Clin. Invest.*, supra.) We describe this in more detail below. Because the transfected cells were non-human, those producing human ELAM polypeptides did so in substantially purified form and essentially free of normally associated animal proteins. We picked cells which tested positive in this assay, collected the plasmid DNA, and isolated the inserts from them. These inserts contain DNA sequences encoding ELAM1.

In a second method, we identified cDNA inserts from the enriched sublibrary which hybridized on a Northern blot to a 4 kb band of induced, but not uninduced, mRNA. Two of these inserts contained DNA sequences for ELAM1. Other inserts from the sublibrary encode different induced mRNAs.

Using the clones identified by these two methods we determined the sequence of ELAM1 cDNA. It should be noted that due to the degeneracy of the genetic code one may alter many of the nucleotides of this sequence and retain a DNA sequence that, when in proper reading frame and operatively linked to an expression control sequence, codes on expression for an amino acid sequence identical to that encoded by the DNA sequence we have presented in FIGS. 1A–1E. It should be clear that DNA sequences for fragments of the ELAM1 cDNA sequence, or DNA sequences which are substantially homologous to the ELAM1 cDNA sequence and which themselves encode ELAM polypeptide would hybridize to the disclosed ELAM1 cDNA sequence under standard hybridization conditions.

We used the DNA sequence to deduce the amino-acid sequence of ELAM1. It should be clear that given the current state of the protein-engineering art, an artisan could make purposeful alterations in this amino-acid sequence and still retain a molecule with activity, biological or immunological, similar to that of the molecule we have disclosed herein.

We have also isolated a MILA, CDX, which is involved in ELAM1-mediated adhesion. This involved, as a first step, the production of monoclonal antibodies against the molecule. We immunized mice with whole HL-60 cells, a PMN-related cell line, which we knew bound to ELAM1. However, one could immunize with any cell line which binds to ELAM1, including PMNs themselves and, as we shall show, monocytes and U937 cells. After finding that immune serum from these animals inhibited binding of HL-60 cells to HUVECs in the adhesion assay we will describe, we created hybridomas from spleen cells in a manner well known to the art. (*Monoclonal Antibodies: Principles and Practice*, J. W. Goding, ed., Academic Press, New York (1983).) Then we identified those hybridomas which produced Moabs against CDX by testing their ability in the adhesion assay to inhibit binding of HL-60 cells to induced HUVECs. We used several of these hybridomas to produce ascites fluid containing monoclonal antibodies.

Monoclonal antibodies against CDX possess the following characteristics: First, they inhibit binding of HL-60 cells or PMNs to cells which express ELAM1. Second, these antibodies exhibit a specific cell-binding pattern: they recognize cells which bind to ELAM1, but they do not recognize cells which - do not bind to ELAM1. Third, they have a recognition pattern for human cell lines that is distinct from the pattern of antibodies against other cell-surface molecules, such as α-LFA-1, α-LFA-3, α-p80, α-ICAM, and α-CD4.

We used these Moabs to isolate CDX. We radioactively labelled HL-60 cell-surface proteins using a modification of a method described by Kurzinger. (Kurzinger, K., et al., "A Novel Lymphocyte Function-Associated Antigen (LFA-1): Cellular Distribution, Quantitative Expression, and Structure," *J. Immunol.*, 127, p. 596 (1981).) We solubilized the membrane proteins and incubated them with an α-CDX monoclonal. Then we isolated the bound molecules. These molecules appear on SDS-PAGE as a single, diffuse band of about 175 kD. This molecule is CDX isolated substantially free of normally associated animal proteins.

One can also isolate a DNA sequence which codes on expression for CDX using techniques known to the art. Some practical techniques involve using expression systems to express cloned DNA. As we have mentioned, a variety of eukaryotic expression systems are available. We have created a cDNA library from RNA of a cell line which expresses CDX, HL-60. We are enriching this library for CDX DNA sequences by using subtraction techniques, as we have described, with a cell line which does not express CDX, such as HeLa cells. We have transfected a cell line, COS 7, with both the whole library and the subtracted library. We are identifying those cells expressing CDX in a number of ways. Functional cones may be identified by transient expression in, e.g., COS 7 cells, as we will describe.

First, we are incubating the transfected cells with the α-CDX Moabs and panning them on plates coated with antimouse IgG or IgM. Cells which bind to the plate will be those expressing CDX. This method requires several rounds of isolating the plasmid DNA, retransfecting cells, and panning.

Second, we are taking advantage of fluorescent-antibody labelling. In this method, CDX-expressing cells are incubated with α-CDX Moabs and then the Moabs are labelled with fluoroescently tagged antimouse antibody. One may then sort cells binding the fluorescent antibodies with a fluorescence activated cell sorter (FACS). The DNA from the sorted cells may be used to transform a bacterial host such as *E. coli*. DNA from the resulting colonies may be used to transfect COS 7 cells, and this procedure may be repeated until a single CDX-expressing clone is identified.

Third, we may create an expression library in *E. coli*. For example, we could construct a λZAP/HL-60 library and use it to express the inserted DNA in *E. coli*. After plating, one could screen the plaques directly with radioactively labelled α-CDX monoclonals. (Yound and Davis, *Science*, supra, Young and Davis, *Proc. Natl. Acad. Sci., USA*, supra.) Then one could pick the plaques to which the monoclonals bind and isolate the DNA insert from them.

Another method we are using to identify the ELAM1 ligand, not based on antibody recognition, is to use a subtracted library to transfect COS 7 cells and then pan them directly onto ELAM-expressing cells (such as induced HUVECS, ELAM-expressing COS 7 cells, or ELAM-expressing CHO cells.) Once again, multiple rounds of panning are required to enrich the library sufficiently to isolate the pertinent clones.

Another technique for isolating DNA sequences involves screening a cDNA library with oligonucleotide probes. If sufficient purified protein is available, one could determine its amino acid sequence and synthesize oligonuleotide probes which encode at least a portion of it. These probes could then be used to screen the cDNA library.

Although we have isolated CDX, one should recognize that in light of our disclosure the practitioner is not limited to this example. The invention also contemplates isolation of other MILAS by using as an antigenic source cells which do not bind to cytokine-induced endothelium via ELAM1. For example, one could raise antibodies against lymphocytes which bind to IL-1-induced HUVECs about twenty-four hours after stimulation but do not bind via ELAM1. Then one could test these antibodies for inhibition in an adhesion assay similar to one we describe and use inhibiting antibodies to isolate other MILAs. Similarly, one could isolate DNA sequences which code on expression for these MILAs as we describe.

Several uses for ELAM and MILA DNA sequences and molecules are contemplated in the present invention. First, one could use ELAMs and MILAs to produce monoclonal antibodies which are reactive for these molecules. The Moabs may be used in turn as therapeutic agents to inhibit leukocyte binding to endothelial cells.

Second, one could use soluble ELAM, soluble ELAM ligand, or fragments of either as binding inhibitors. The ELAM peptides would bind to the ELAM ligand on PMNs, and the ELAM ligand would bind to ELAM on endothelial cells. Both methods would thereby inhibit PMN binding to endothelial cells. To produce soluble ELAM or ELAM ligand one would alter a DNA encoding these molecules to eliminate the transmembrane region. Thus, DNAs for soluble molecules would include all or part of the extracellular domain, perhaps attached to the cytoplasmic domain. This approach has already been validated using soluble CD4, the protein on T-cells which binds to the AIDS virus. (Fisher, R. A., et al., "HIV Infection Is Blocked In Vitro by Recombinant Soluble CD4," *Nature*, 331, pp. 76–78 (1988).) This approach also avoids the problems of antibody therapy, since the protein introduced is less likely to induce a serious immune response.

Third, one could use molecules binding to ELAM (such as anti-ELAM antibodies or markers such as the ligand or fragments of it) to detect inflammation. This could involve, for example, making a molecule detectable by fluorescence or radioactivity, administering it to a patient and determining where in the body it accumulated. In this way one could also identify the type of inflammation. For example, the binding to ELAM1 would indicate acute, as opposed to chronic inflammation.

Fourth, if ELAM binds to its ligand through a carbohydrate moiety or some other post-translational modification, one could use ELAM to identify the carbohydrate on the ELAM ligand to which it bound.

Fifth, one could use ELAMs and MILAs as part of a system to screen small molecules for adhesion inhibitors. For example, one could create an assay system in which small molecules are tested for the ability to inhibit the interaction of CDX and ELAM1.

Finally, one could use these molecules to identify endogenous proteins which inhibit leukocyte binding to ELAMs. We have reason to believe that such molecules exist: Investigators have tentatively identified a molecule, leukocyte adhesion inhibitor (LAI), that is involved in detaching bound PMNs from the endothelium. (Wheeler, M. E., et al., "Cultured Human Endothelial Cells Stimulated with Cytokines or Exdotoxin Produce an Inhibition of Leukocyte Adhesion," *J. Clin. Invest.*, 82, pp. 1211–18, (1988).)

These uses may require, at some stage, the expression of the ELAM and MILA DNA sequences of this invention. As is well known in the art, DNA sequences may be expressed by operatively linking them to an expression control sequence in an appropriate expression vector and employed in that expression vector to transform an appropriate unicellular host.

Such operative linking of a DNA sequence of this invention to an expression control sequence, of course, includes, if not already part of the claimed DNA sequence, the provision of an initiation codon, ATG, in the correct reading frame upstream of the DNA sequence.

A wide variety of host/expression vector combinations may be employed in expressing the DNA sequences of this invention. Useful expression vectors, for example, may consist of segments of chromosomal, non-chromosomal and synthetic DNA sequences, such as various known derivatives of SV40 and known bacterial plasmids, e.g., plasmids from *E.coli* including col E1, pCR1, pBR322, pMB9 and their derivatives, wider host range plasmids, e.g., RP4, phage DNAs, e.g., the numerous derivatives of phage λ, e.g., NM989, and other DNA phages, e.g., M13 and *Filamenteous* single stranded DNA phages, yeast plasmids such as the 2μ plasmid or derivatives thereof, vectors useful in eukaryotic cells, such as vectors useful in animal cells and vectors derived from combinations of plasmids and phage DNAs, such as plasmids which have been modified to employ phage DNA or other expression control sequences.

In addition, any of a wide variety of expression control sequences—sequences that control the expression of a DNA sequence when operatively linked to it—are used in these vectors to express the DNA sequence of this invention. Such useful expression control sequences, include, for example, the early and late promoters of SV40 or the adenovirus, the lac system, the trp system, the TAC or TRC system, the major operator and promoter regions of phage λ, the control regions of fd coat protein, the promoter for 3-phosphoglycerate kinase or other glycolytic enzymes, the promoters of acid phosphatase, e.g., Pho5, the promoters of the yeast α-mating factors, and other sequences known to control the expression of genes of prokaryotic or eukaryotic cells or their viruses, and various combinations thereof.

A wide variety of unicellular host cells are also useful in expressing the DNA sequences of this invention. These hosts may include well known eukaryotic and prokaryotic hosts, such as strains of *E.coli, Pseudomonas, Bacillus, Streptomyces,* fungi such as yeasts, and animal cells, such as CHO and R1.1, B-W and L-M cells, African Green Monkey kidney cells, such as COS 1, COS 7, BSC1, BSC40, and BMT10, and human cells and plant cells in tissue culture.

It should of course be understood that not all vectors, expression control sequences and hosts will function equally well to express the DNA sequences of this invention. Neither will all hosts function equally well with the same expression system. However, one of skill in the art may make a selection among these vectors, expression control sequences, and hosts without undue experimentation and without departing from the scope of this invention. For example, in selecting a vector, the host must be considered because the vector must function in it. The vector's copy number, the ability to control that copy number, and the expression of any other proteins encoded by the vector, such as antibiotic markers, should also be considered.

In selecting an expression control sequence, a variety of factors should also be considered. These include, for example, the relative strength of the system, its controllability, and its compatibility with the particular DNA sequence, of this invention, particularly as regards potential secondary structures. Unicellular hosts should be selected by consideration of their compatibility with the chosen vector, the toxicity of the product coded on expression by the DNA sequences of this invention to them, their secretion characteristics, their ability to fold proteins correctly, their fermentation requirements, and the ease of purification of the products coded on expression by the DNA sequences of this invention.

Within these parameters one of skill in the art may select various vector/expression control system/host combinations that will express the DNA sequences of this invention on fermentation or in large scale animal culture, e.g., mouse cells or CHO cells.

In order that one may better understand this invention we set forth the following examples. These examples are for purposes of illustration and are not to be construed as limiting the scope of the invention in any manner.

EXAMPLE I

PREPARATION OF A cDNA SUBLIBRARY ENRICHED FOR ELAM SEQUENCES

We prepared a cDNA sublibrary enriched for ELAM1 as follows:

We isolated human umbilical vein endothelial cells (HUVECs) from umbilical cords, grew them in primary culture, and serially passaged them as described in Gimbrone. (Gimbrone, M. A., Jr., "Culture of Vascular Endothelium", *Prog. Hemostasis Thromb.*, 3, pp. 1-28 (1976).) We used HUVECs for library construction at passages 4 or 5. To induce the cells to produce mRNA for ELAM we incubated confluent monolayers for 2.5 hours at 37° with recombinant human IL-1β (10 units/ml). We isolated the mRNA from these cells and reverse-transcribed it into cDNA with techniques well known to the art. (Gubler and Hoffman, supra.) Using standard procedures, we ligated double stranded cDNA to a NotI-BstXI linker/adaptor having the following sequence:

5' GCG GCC GCT TTA GAG CAC A 3'

3' CGC CGG CGA AAT CTC 5'

We then size-selected the cDNA on a 4.2 ml 5–20% potassium acetate gradient, 2 mM EDTA, 1 μg/ml ethidium bromide, in a Beckman SW60 Rotor for 3 hours at 50,000 rpm at 22° C. according to the protocols of Brian Seed. Maniatis, supra, p. 278. We pooled the cDNA fragments of greater than 500 base pairs. Then we prepared the vector, pCDM8. We digested this plasmid with BstXI. To remove the 400 base pair stuffer fragment we centrifuged the mixture on a potassium acetate gradient, as above, and isolated the large fragment. We further purified this fragment by agarose gel electrophoresis, and then ligated the cDNA to the vector. In this way we created recombinant DNA molecules containing DNA sequences for mRNA expressed in induced HUVECs. We used these plasmids to transform *E.coli* MC1061 P3. The result was a collection of over $7 \times 10^6$ recombinant clones comprising a cDNA library for IL-1β-induced HUVEC mRNA.

In order to prepare from the cDNA library a sublibrary enriched for ELAM1 cDNA sequences, we first prepared a subtracted probe enriched for ELAM1 sequences. We prepared cDNA as above from HUVECs induced with IL-1β and labelled it with $^{32}P$ (Davis, supra.) Then we isolated mRNA from HUVECs which had not been induced. To subtract uninduced cDNA sequences from induced sequences we hybridized the mRNA with the cDNA and isolated cDNA which had not hybridized to mRNA, as described by Davis, supra. We subjected the isolated cDNA to another round of subtraction to increase the level of enrichment. In all, we prepared three batches of subtracted probes enriched for ELAM sequences.

We tested the level of purification of the probe by Northern blot. (Lehrach et al., "RNA Molecular Weight Determinations by Gel Electrophoresis Under Denaturing Conditions," *Biochem.*, 10, pp. 4743-51 (1977).) We ran a gel with parallel lanes of polyA+mRNA from induced and uninduced HUVECs and blotted it on Gene Screen (New England Nuclear). Hybridization and subsequent autoradiography revealed that the probe bound strongly to a 4 kb band in the induced lane but not did not bind, beyond background, to the uninduced lane. Occasionally we noted less intense hybridization bands to other messages in the induced lane.

We used the subtracted probe to create a cDNA sublibrary enriched for IL-1-induced sequences. We began by plating-out one million clones of the IL-1β-induced HUVEC cDNA library. We plated one million colonies on Gene Screen Plus filters (New England Nuclear) on LB agar containing 12.5 μg/ml ampicillin and 7.5 μg/ml tetracycline, and grew them at 37° C. for 12 hours. We made two replicate filters (lifts) from each master. We grew these on LB agar containing 12.5 μg/ml ampicillin and 7.5 μg/ml tetracycline for 4-6 hours and amplified them on LB agar containing 250 μg/ml chloramphenicol for 16 hours. We lysed the filters according to manufacturer's protocol and then prehybridized them in Plaque Screen Buffer (0.05M TRIS-HCl pH7.5, 1M NaCl, 1% SDS, 0.1% sodium pyrophosphate, 0.2% polyvinylpyrolidone (PVP), 0.2% Ficoll-400, 0.2% BSA). We hybridized the filters at 65° C. for 40 hours in 50 ml Plaque Screen Buffer containing 10% dextran sulfate and 100 μg/ml yeast tRNA and approximately $1 \times 10^7$ cpm of the subtracted IL-1β-induced HUVEC cDNA. We then washed the filters twice with Plaque Screen Buffer, twice with 2x SSC, 1% SDS, and twice with 1x SSC, 1% SDS at 65°. We then exposed the filters to film for 5 days.

We selected colonies that hybridized to the probe by aligning the master filters with the autoradiographs and scraping the colonies off the filters with toothpicks. We placed each scraping in one well of a 96-well microtiter plate filled with LB both containing 7.5 μg/ml tetracycline or 12.5 μg/ml ampicillin. After inoculation, we incubated the microtiter plates overnight at 37° C. When the cells had grown we added glycerol to each well to a final concentration of 20% and stored the plates at −70° C. In this way we isolated from the master library filters 864 colonies comprising the cDNA sublibrary enriched for ELAM sequences. We point out that because of the plating density, not all the colonies of the enriched library were pure.

We carried out two sets of procedures in parallel with the enriched cDNA sublibrary.

EXAMPLE II

ISOLATION OF A CLONE EXPRESSING ELAM1

In a first procedure we isolated from the enriched sublibrary a clone which expressed ELAM1. We cloned the original cDNA library into an animal cell expression vector, pCDM8. We chose to transfect this sublibrary into a cell line competent for highlevel transient expression, the African Green Monkey kidney cell line, COS 7. We plated the cells and transfected the sublibrary by spheroplast fusion. (Sandri-Goldin, R. M., et al., "High Frequency Transfer of Cloned Herpes Simplex Virus Type I Sequences to Mammalian Cells by Protoplast Fusion," *Molec. and Cell Biol.*, 1, pp. 743-52 (1981).) Forty-eight hours after transfection, we assayed the COS 7 cells for expression of ELAM1 by their ability to bind HL-60 cells, a cell line known to bind to endothelial cells induced with inflammatory agents.

We performed the assay as follows: We labelled HL-60 cells with carboxyflourescein diacetate according to Brenan's and Parish's method (Brenan, M. and C. R. Parish, "Intracellular Fluorescent Labelling of Cells for Analysis of Lymphocyte Migration," *J. Immun. Meth.*, 74, pp. 31-38 (1984)). Briefly, we resuspended HL-60 cells in RPMI/10% FCS at a concentration of $1 \times 10^7$ cells/ml, and added carboxyfluorescein diacetate to a final concentration of 0.1 mg/m]from a stock solution of 10 mg/ml in acetone. We incubated COS 7 cells with labelled HL-60 cells for 15 minutes at room temperature. We washed the cells 3-4 times with RPMI/1% FCS. We examined the petri dish by fluorescence microscopy for clusters of adherent HL-60 cells. We picked regions of the cell plates with clusters of HL-60 cells and lysed the cells 0.6% SDS, 10 mM EDTA, pH 8. Then, we rescued the plasmids according to the method of Hirt. (Hirt, B., "Selective Extraction of Polyoma DNA from Infected Mouse Cell Cultures," *J. Mol. Biol.*, 26, p. 365-69 (1967).) We transformed these pooled plasmids into *E.coli* MC1061 P3. We grew colonies from these transformants and performed a second round of spheroplast fusion with COS 7 cells with subsequent assay for HL-60 adhesion. From among the cells which showed positive for adhesion we selected one and isolated the plasmid from it. We designated this plasmid ELAM pCDM8 clone 6. We deposited this plasmid with In Vitro International, Linthicum, Md., USA on Apr. 20, 1989. It is identified as:

ELAM pCDM8 clone 6/*E. coli* MC1061 P3
Accession Number IVI-10204

On Jun. 20, 1991, we transferred the deposit from In Vitro International, Inc. to the American Type Culture Collection, Rockville, Md., USA in accordance with the Budapest Treaty on the International Recognition of the Deposit of Microorganisms for the Purposes of Patent Procedure. ELAM pCDM8 clone 6, *E. coli* MC1061 P3, IVI-10204, was assigned accession number ATCC 68790.

EXAMPLE III

ISOLATION OF cDNA INSERTS FOR ELAM1 SEQUENCES

In a second procedure, we isolated oDNA inserts for IL-1-induced cDNA sequences. We selected at random twenty-four of the 864 colonies of the enriched library and isolated plasmids from them using the miniprep procedure of Maniatis, supra. We digested the plasmid DNA with XhoI or NotI and separated the fragments on 1% agarose gels. We identified from this gel two plasmids with inserts of greater than 3 kb, isolated these inserts and labelled them with $^{32}P$ (Feinberg, A. P., and B. Vogelstein, "A Technique for Radiolabeling DNA Restriction Endonuclease Fragments," *Anal. Biochem.*, 132, pp. 66-13 (1983) and addendum, *Anal. Biochem.*, 137, pp. 266-67 (1984).)

Then we performed Northern blots with these inserts, as described above. Both inserts hybridized to bands at 4 kb in the induced HUVEC mRNA lane but did not hybridize to the uninduced HUVEC mRNA lane. We subcloned these inserts into NotI-digested pNN11 that had been treated with calf intestinal alkaline phosphatase. We constructed the sequencing plasmid pNN11 by removing the synthetic polylinker from the commercially available plasmid pUC8 (Pharmacia PL Biochemicals) by restriction digestion and replacing it with a new synthetic segment. The 2.5 kb backbone common to the pUC plasmids, which provides an origin of replication and confers ampicillin resistance, remained unchanged. The novel synthetic portion of pNN11 is shown in FIG. 2. We called these new constructs pSQ148 and pSQ149, respectively.

EXAMPLE IV
A DNA SEQUENCE FOR ELAM

We determined the entire DNA sequence for the inserts of plasmids pSQ148 and pSQ149 and 624 nucleotides of the sequence at the 5' end of the insert of ELAM pCDM8 cone 6. We used the Maxam-Gilbert method. (Maxam A., and W. Gilbert, "Sequencing End-Labeled DNA with Base-Specific Chemical Changes," *Methods in Enzymology*, 65, pt. 1, pp. 497-559 (1980).) Because the sequences have significant overlap, we obtained a composite sequence of ELAM cDNA, a sequence of 3863 nucleotides. This sequence consists of 140 nucleotides of the 5' untranslated region, 1830 nucleotides encoding 610 amino acids, and 1893 nucleotides of the 3' untranslated region (including a translational stop codon, a polyadenylation signal and six nucleotides of the polyA tail). We present the cDNA sequence of ELAM1 in FIGS. 1A-1E.

A search of the Genbank Data Base, release 58, December 1988, revealed that the DNA sequence for ELAM has no significant homologies to known DNA sequences.

We used this cDNA sequence to deduce the amino acid sequence of ELAM1 and also present this in FIGS. 1A-1E. Our analysis of the sequence revealed the following properties. The protein possesses a hydrophobic N-terminal sequence characteristic of a signal sequence. (von Heijne, G., "A Method for Predicting Signal Sequence Cleavage Sites," *Nucl. Acids Res.*, 14, pp. 4683-90 (1986).) We have not yet determined the signal cleavage site and the mature N-terminus through protein sequencing. However, based on von Heijne, we predict that the mature N-terminal amino acid will be tryptophan, at nucleotide number 204 in FIG. 1A. The extracellular domain of the polypeptide is approximately 554 amino acids including the signal sequence and is followed by a hydrophobic transmembrane region of 24 amino acids. The protein possesses a short, charged cytoplasmic tail of 32 amino acids. We note that the protein is cysteine-rich and contains eleven potential glycosylation sites.

When we compared the amino acid sequence of ELAM1 to other proteins in the NBRF and NEW protein data bases we found significant homology with several proteins, including complement C2 precursor, β-2-glycoprotein I, C4b-binding protein, complement factor B, complement factor H, Drosophila notch protein, the IgE receptor Hepatic lectin, and Coagulation factors IX and X precursors. Thus, we can divide ELAM into at least three domains based on homology to the above-mentioned proteins: (1) a lectin-like domain (nucleotides 204-563 of FIG. 1A); (2) an EGF-like domain (nucleotides 564-668 of FIG. 1A); and (3) a consensus cysteine repeat unit of 59-63 amino acids containing six cysteine residues per repeat (nucleotides 669-1793 of FIGS. 1A-1C). Other invariable amino acids in each repeat are proline, glycine, and tryptophan.

EXAMPLE V
DNA SEQUENCES FOR OTHER ELAMS

We are also isolating DNA sequences for other ELAMs. ELAM mRNA expression should approximately coincide with the timing of leukocyte infiltration into the extravascular space. PMN infiltration reaches its peak between two-and-one-half to four hours after an inflammatory stimulus. Therefore, to isolate ELAM1, we collected mRNA from HUVECs at two-and-one-half hours after induction with IL-1β. Lymphocyte and monocyte infiltration peak about twenty-four hours after induction. Therefore, to isolate ELAMs for lymphocytes and monocytes we are collecting mRNA around twenty-four hours after induction. From this point we will isolate the ELAM cDNA sequences in a manner similar to the one we used to isolate the cDNA sequence for ELAM1.

Alternatively, one could identify other ELAMs by inducing cells with other inflammatory agents, such as TNF, LT, or LPS.

EXAMPLE VI
ANTIBODIES RECOGNIZING CDX

We isolated CDX, a MILA involved in ELAM1-mediated binding. As a first step we prepared monoclonal antibodies against it. We directed our work toward producing antibodies which recognized an antigen on the leukocyte cell surface and which interfered with leukocyte-endothelial cell binding. Furthermore, in order to assure that the antigen which these monoclonals recognized was involved in ELAM1-mediated adhesion, we tested the monoclonals in systems in which ELAM1-mediated binding was the exclusive cell-cell binding pathway.

1. Preparation and Analysis of Monoclonal Antibodies Against CDX a. Adhesion assay To identify Moabs which inhibit leukocyteendothelial cell binding, we developed an improved assay to detect endothelial cell-leukocyte adhesion. We performed this assay using HL-60 cells and HUVECs. It should be clear the one can perform such an assay using any cell line which expresses a MILA and with any cell line that expresses an ELAM. In 48-well tissue-culture plates we grew HUVECs to confluence. ($8 \times 10^4$ cells/well). We washed the cells once with RPMI/1% FCS and added 0.5 ml RPMI/1% FCS with 13 U/ml of IL-1β to each well (except the control wells). We incubated these cells for 4 hours at 37° C. Just before use, we washed them once with RPMI/1% FCS. The HL-60 cells which we used in the assay had been labeled overnight with 1 μCi/ml of $^{35}$S-methionine. We washed these cells once and then resuspended them in RPMI/1% FCS at $5 \times 10^6$ cells/ml. We took 100 μl of the HL-60 cells and incubated them for 30 min. at 0° C. with 50 μl of Moab (1 μg/ml). Then we added the 150

μl to each well of HUVECs. We allowed the cells to bind for 10 min. at 20° C. and then washed the wells gently once with RPMI/1% FCS. We filled the wells with RPMI/1% FCS, sealed the plates, inverted them, and centrifuged them for 2 min. at 500×g. We removed the media and washed the wells two more times with PBS−−. (PBS−− is PBS without Ca++ and without Mg++.) We determined the number of HL-60 cells bound to the HUVECs by solubilizing the cells in each well with 200 μl of 0.2N NaOH/1% SDS, adding 4.5 ml of scintillant (Ready Protein, Beckman), and counting with a scintillation counter.

b. Preparation of hybridomas

To make monoclonal antibodies against CDX we prepared hybridomas in the following manner. We injected BALB C mice with whole, live HL-60 cells. Initially, each mouse received $2 \times 10^7$ cells in PBS−− intraperitoneally (IP). We injected complete Freund's adjuvant intraperitoneally at a different site 2–24 hours later. We boosted the mice with $2 \times 10^7$ cells IP every second week for six weeks. Four days before fusing we injected the mice intravenously with $5 \times 10^6$ cells and IP with $5 \times 10^6$ cells.

We tested immune serum from these animals for the ability to inhibit binding of the HL-60 cells to IL-1β stimulated HUVECs by the adhesion assay described above. The immune serum tested positive after the third boost and we proceeded to produce hybridomas from the spleen cells of the immunized animals. We performed fusion of spleen cells and myeloma cells in a manner standard to the art.

(Monoclonal Antibodies Principles and Practice, supra).

Using the adhesion assay we described above, we screened the hybridomas for those producing monoclonal antibodies which inhibited the binding of HL-60 cells to IL-1β-induced HUVECs. In this way we identified hybridomas which produced monoclonal antibodies which recognized CDX. We used five of these hybridomas to produce ascites fluid. We deposited one of them, designated SGB$_3$B$_4$, with In Vitro International on Apr. 25, 1989. It is identified as:

SGB$_3$B$_4$
Accession number: IVI-10205

On Jun. 20, 1991, we transferred the deposit from In Vitro International, Inc. to the American Type Culture Collection, Rockville, Md., USA in accordance with the Budapest Treaty on the International Recognition of the Deposit of Microorganisms for the Purposes of Patent Procedure. Hybridoma SGB$_3$B$_4$, IVI-10205, was assigned accession number ATCC HB 10879.

c. FACS analysis

To identify to which cell types our monoclonals bound, we performed FACS analysis. This involved taking $2 \times 10^5$ cells, washing them one time with PBS−−, and then blocking Fc receptors by incubation in 25 μl of RPMI, 1% FCS, 0.1 mg/ml human IgG, and 0.1% sodium azide for 10 min. at 0° C. We then added antibody (25 μl at 1 μg/ml) and incubated the cells 30 min at 0° C. We centrifuged the cells at 1000×g for 5 min., washed them two times with Buffer A (PBS−−, 5% FCS, 0.1% azide) and resuspended them in 25 μl Buffer A containing 0.1 mg/ml human IgG. We added fluorescine-conjugated anti-mouse IgG (25 μl at 5 μg/ml in Buffer A (Cappel)) and incubated the mixture 30 min at 0° C. We centrifuged the cells, washed them once with Buffer A, and resuspended them in 250 μl Buffer A. Then we analyzed them on a Beckton-Dickinson FACStar Cell Sorter.

We performed cell binding studies with the ELAM-expressing COS cells essentially as described for the HL-60 cell-HUVEC adhesion assay.

2 Demonstration that Hybridoma SGB$_3$B$_4$ Produced Monoclonal Antibodies Which Recognize CDX We have developed several lines of evidence that demonstrate the specific recognition of monoclonals from hybridoma SGB$_3$B$_4$ for a MILA involved in ELAM1-mediated binding, specifically, CDX.

First, the α-CDX antibodies should inhibit binding of cells expressing CDX to ELAM1-expressing cells. Using the adhesion assay, we showed that these monoclonals do indeed inhibit the binding of HL-60 cells and PMNs to IL-1β-induced HUVECs and ELAM1-expressing COS 7 cells. The only binding pathway for HL-60 cells and PMNs which is utilized in ELAM1-expressing COS 7 cells is ELAM1 itself. Therefore, antibody inhibition of cell-cell adhesion in this system must be through the ELAM1 pathway via CDX.

Second, α-CDX monoclonals should recognize those cells which bind to ELAM1-expressing cells in an adhesion assay, but should not recognize those cells which do not bind to ELAM1 in this assay. Using FACS analysis, we determined the binding pattern of our Moabs. These monoclonals bound to the following cell types HL-60, U937, HT-29, PMNs, and monocytes. They did not bind to these cells: RAJI, DAUDI, RAMOS, HeLa, T-cells, or B-cells. (We isolated the non-transformed cells by fractionating peripheral blood leukocytes.) This binding pattern precisely parallels the binding of these cells to ELAM1-expressing COS 7 cells.

Third, α-CDX monoclonals should exhibit a different recognition pattern than monoclonals against other leukocyte cell-surface antigens, such as LFA-1, LFA-3, p80, ICAM1 and CD4. In fact, no other monoclonal of which we are aware exhibits the same cell-recognition pattern as our antibodies.

In sum, it is apparent that the monoclonals produced by hybridoma SGB$_3$B$_4$, and by other hybridomas we isolated, recognize CDX. Consequently, we used these monoclonals to isolate CDX, itself.

EXAMPLE VII

ISOLATION OF CDX

1. Iodination of HL-60 Cell Surface Proteins

We washed $2 \times 10^7$ HL-60 cells three times with PBS−−, resuspended them in 0.5 ml. PBS−− and added them to a tube coated with 100 μg. (1,3,4,6-tetrachloro-3α, 6α-diphenylglycouril (Sigma Chemical Co.).) To this we added 1 mCi of $^{125}$I. We incubated the mixture for 30 min at 0° C. We quenched the reaction with cold tyrosine and then cold NaI. We transferred labelled cells to a tube containing 10 ml of RPMI/10% FCS and centrifuged them at 1000×g for 5 min. Then we washed them first with another 10ml of RPMI/10% FCS and second with 2 ml of PBS=We lysed the cells by addition of 1.0 ml PBS=containing 1% NP40, 2 mM PMSF, 1 mM EDTA, soybean Trypsin inhibitor (50 mg/ml), and Leupeptin (1 mM) (Sigma Chemical Co.) Then we incubated them for 30 min at 0° C. We centrifuged the lysate for 10 min at 10,000×g to remove particulate matter. We precleared the supernatant containing labelled solubilized membrane proteins with 10 μg of rabbit anti-mouse IgM (Jackson Immuno- Research Labs) and 50 μl of protein G sepharose (Zymed, 2 mg protein G/ml) for 1 hour at 0° C. We stored the lysate at 4° C.

2. Immunoprecipation of CDX

We purified CDX away from the other labelled proteins using the Moabs to immunoprecipitate it. We performed the immunoprecipitation as follows:

We incubated precleared lysate (50-100 μl) with 5 μg of α-CDX monoclonals for 2 hours at 4° C. Then we added 10 μg of Rabbit-anti-mouse IgM and incubated the lysate for another hour at 4° C. To precipitate molecules bound to these antibodies, we added Protein G Sepharose (10 μl) and rocked the mixture for 16 hours at 4° C. We washed the Sepharose four times with 2 ml PBS−− containing 0.5% NP40, 0.5% DOC, and 1 mM EDTA. Then we resuspended the sample in SDS sample buffer containing β-ME. We heated the sample for 10 min at 85° C. and separated the molecules on a 10% SDS polyacrylamide gel. We dried the gel and autoradiographed it.

CDX appeared on the autoradiograph as a single, diffuse band with molecular weight of approximately 175 kD.

EXAMPLE VIII

SMALL MOLECULE SCREENING

One can use ELAM and its ligand in three basic adhesion assays to screen for potential small molecule inhibitors of adhesion, such as synthetic organic chemicals, natural fermentation products, peptides, etc.:

1. Cell-Cell Adhesion Assays

A first assay would test the ability of small molecules to inhibit cell-cell adhesion. One could perform this assay in 96-well microtiter plates. One would plate-out a transfected cell line that stably expresses ELAM and then add HL-60 cells in the presence of small molecules. Inhibitors are identified by their ability to inhibit HL-60 binding to the ELAM-expressing cells. One would perform an assay exactly as described for screening for monoclonal antibodies to the ELAM ligand.

2. Cell-Adhesion Protein Assays

A second assay would test the ability of a small molecule to inhibit cell binding to ELAM itself. One would bind ELAM, preferably in soluble form, to the wells of 96-well plates, generating plates with immobilized ELAM in each well. One would perform adhesion assays as in example 1, above. One would identify inhibitors by their ability to inhibit HL-60 binding to the plate. Alternatively, one could use the ELAM ligand in this assay, using as the probe a cell line that stably expresses ELAM.

Another alternative assay in this category would examine the binding of soluble ELAM or ELAM ligand to monolayers of cells stably expressing ELAM ligand or ELAM, respectively. The soluble molecule would be labelled with a reporter group (e.g., radioactivity, fluorescent probe, enzyme, etc.)

3. Adhesion Protein-Adhesion Protein Assays

This assay tests the ability of a small molecule to inhibit the binding of ELAM to its ligand. One of the two molecules in soluble form, e.g., soluble ELAM, is immobilized in the wells of a 96-well microtiter plate, and adhesion is measured by binding of the other member of the pair, e.g. ELAM ligand labelled with a reporter group.

In each of these three assays, one detects inhibitors by their ability to inhibit adhesion.

EXAMPLE IX

ISOLATION OF THE ELAM PROMOTER

One may also use the DNA sequences of this invention to isolate the endogenous ELAM expression control sequences, including the ELAM promoter, which controls the transcription of the ELAM gene. These expression control sequences have a number of uses. First, the ELAM promoter would be a useful control sequence in an inducible expression system. As we have described, ELAM expression is induced by cytokines and other macromolecules. Second, a better understanding of how the promoter works could lead to ways to repress it, thereby resulting in means to inhibit ELAM expression on the endothelial cell surface. Third, the expression control sequences would be useful in gene targeting. ELAM expression is specific for cell type—it exists only on the surface of endothelial cells. Therefore, one could operatively link to these sequences genes not normally expressed in endothelial cells, use the recombinant DNA molecules to transform endothelial cells, and express the gene.

We have pursued the following course in the isolation of ELAM expression control sequences. We selected as probes either the entire ELAM pCDMB clone 6 insert or a 400 base pair fragment from its 5' end. We labeled these molecules with $^{32}P$ by random priming. Then we screened human genomic libraries with the ELAM cDNA probes. In this way we isolated genomic clones which hybridized to the ELAM cDNA. Some of these clones hybridized to the subset of the probes corresponding to the 5' end of ELAM cDNA. These clones should contain the expression control sequences, including the promoter.

One may now analyze these clones to identify the expression control sequences. First, one could isolate and subclone potential promoter sequences. Then, one would sequence the clones to locate expression control sequences.

Once isolated, one could test inducibility of the promoter and its strength in binding proteins which bound to DNA, such as DNA polymerase.

While we have hereinbefore described a number of embodiments of this invention, it is apparent that one of skill in the art could alter our procedures to provide other embodiments which utilize the processes and compositions of this invention.

Therefore one will appreciate that the scope of this invention is to be defined by the claims appended thereto rather than the specific embodiments which we have presented by way of example.

We claim:

1. Hybridoma SGB₃B₄, accession number ATCC HB 10879.

2. The monoclonal antibodies produced by hybridoma SGB₃B₄, accession number ATCC HB 10879.

3. A monoclonal antibody recognizing the epitope of CDX recognized by monoclonal antibody SGB₃B₄, accession number ATCC HB 10879.

* * * * *

UNITED STATES PATENT AND TRADEMARK OFFICE
CERTIFICATE OF CORRECTION

PATENT NO. : 5,217,870

DATED : June 8, 1993

INVENTOR(S) : Hession et al.

It is certified that error appears in the above-identified patent and that said Letters Patent is hereby corrected as shown below:

On the title page:

item [75]: "Catherine A. Hession, South Weymouth; Roy R. Lobb, Westwood; Susan E. Goelz, Winchester" should be --Susan E. Goelz, Winchester; Roy R. Lobb, Westwood--.

Item[56] under "OTHER PUBLICATIONS," in line 3 of the Gubler and Hoffman citation: After "263-269" insert --(1983)--.

| Column | Line | |
|---|---|---|
| 1 | 42 | "Thrombasis" should be --Thrombosis--. |
| 5 | 19 | "ncleotides" should be --nucleotides--. |
| 5 | 19-20 | "neucleotides" should be --nucleotides--. |
| 5 | 22 | "CNA" should be --DNA--. |
| 6 | 54 | After "screening" insert -- with labeled cDNA; second, production of subtracted--. |
| 6 | 64 | After "pp." insert --2194-98--. |
| 8 | 58 | After "which" delete hyphen --(-)--. |
| 9 | 20 | "cones" should be --clones--. |
| 9 | 45 | "Yound" should be --Young--. |
| 9 | 61 | "oligonuleotide" should be --oligonucleotide--. |

UNITED STATES PATENT AND TRADEMARK OFFICE
CERTIFICATE OF CORRECTION

PATENT NO. : 5,217,870

DATED : June 8, 1993

INVENTOR(S) : Hession et al.

It is certified that error appears in the above-identified patent and that said Letters Patent is hereby corrected as shown below:

| Column | Line | |
|---|---|---|
| 14 | 22 | "0.1 mg/m]" should be --0.1 mg/ml--. |
| 14 | 58 | "oDNA" should be --cDNA--. |
| 17 | 7 | "PBS--", first and second occurrences, should be --PBS$^=$--. |
| 17 | 17 | "PBS--", first and second occurrences, should be --PBS$^=$--. |
| 17 | 57 | "PBS--" should be --PBS$^=$--. |
| 17 | 62 | "PBS--" should be --PBS$^=$--. |
| 18 | 51 | "PBS--", first and second occurrences, should be --PBS$^=$--. |
| 19 | 15 | "PBS--" should be --PBS$^=$--. |

Signed and Sealed this

Sixteenth Day of August, 1994

Attest:

BRUCE LEHMAN

*Attesting Officer*   *Commissioner of Patents and Trademarks*